United States Patent [19]

Takahara et al.

[11] Patent Number: 5,441,735

[45] Date of Patent: Aug. 15, 1995

[54] METHOD FOR CONTROLLING SOFT ROT, BACTERIAL SEEDLING BLIGHT OF RICE AND BLACK ROT

[75] Inventors: Yoshiyuki Takahara, Saitama; Tetsuya Iwabuchi, Kawagoe; Masayuki Shiota, Saitama, all of Japan

[73] Assignee: Central Glass Co., Ltd., Ube, Japan

[21] Appl. No.: 82,675

[22] Filed: Jun. 25, 1993

[30] Foreign Application Priority Data

| Jul. 31, 1992 | [JP] | Japan | 4-205624 |
| Jul. 31, 1992 | [JP] | Japan | 4-205625 |
| Sep. 9, 1992 | [JP] | Japan | 4-241015 |
| Apr. 27, 1993 | [JP] | Japan | 5-101192 |

[51] Int. Cl.$^6$ .............. A01C 1/08; A01N 63/00; C12M 1/04; C12N 1/22
[52] U.S. Cl. .............. 424/93.2; 424/93.1; 424/93.4; 435/29; 435/30; 435/172.1; 435/252.1; 47/57.6
[58] Field of Search ............ 424/93 A, 93.1, 93.2, 424/93.4; 435/30, 29, 172.1, 252.1; 47/57.6, DIG. 9, DIG. 10

[56] References Cited

U.S. PATENT DOCUMENTS

| 4,849,008 | 7/1989 | Schroth et al. | 71/77 |
| 4,855,230 | 8/1989 | Lindow | 435/30 |

FOREIGN PATENT DOCUMENTS

| 3101606 | 4/1991 | Japan . |
| 4179475 | 6/1992 | Japan . |

OTHER PUBLICATIONS

Tatsuo Ishikawa (ed.); *Experimental Methods in Microbial Genetics*, pp. 3–32, Tokyo, Kyoritsu–Shuppan (1982).

Masao Goto, *New Plant Bacterial Pathogenesis*, p. 166, Tokyo, Soft Science (1981).

Hiroyuki Tsuyama, *Shokubutsu Boeki* (Plant Protection), vol. 34, pp. 294–298 (1980).

Yoshiyuki Takahara, *Shokubutsu Boeki* (Plant Protection), vol. 46, pp. 484–487 (1992).

Endo et al., *Ann. Phytopath. Soc. Japan*, vol. 41, pp. 40–48 (1975).

Itoh et al., *J. Gen. Appl. Microbiol.*, vol. 24, pp. 27–39 (1978).

Carlton and Brown, "Gene Mutation," in Gerhardt et al. (eds.), *Manual of Methods for General Bacteriology*, pp. 223–242, American Society for Microbiology, Washington, D. C. (1981).

Davison. 1988. Bio/Technology. 6:282–286.

Cullen et al. 1986. Tibtech. May. 115–119.

Pirhonen et al. 1991. Molecular Plant–Microbe Interactions. 4(3):276–283.

Jayaswal et al. 1985. Journal of Bacteriology. 164(1):473–476.

*Primary Examiner*—David T. Fox
*Assistant Examiner*—Erich E. Veitenheimer
*Attorney, Agent, or Firm*—Pennie & Edmonds

[57] ABSTRACT

A microbial pesticide containing a living *Erwinia carotovora* subsp. *carotovora*, particularly, the *Erwinia cartovora* subsp. *carotovora* CGE234M403 strain, from which the pathogenicity of soft rot is deleted by mutagenesis and which is immobilized by mixing with a saccharide such as saccharose, glucose, fructose or sorbitol or beef extract and drying or freeze-drying the mixture under reduced pressure, as an active ingredient is applied to soil or plants, which are liable to suffer from soft rot, bacterial seedling blight of rice and black rot, in the form of a suspension, granules or powder to control the diseases.

17 Claims, No Drawings

METHOD FOR CONTROLLING SOFT ROT, BACTERIAL SEEDLING BLIGHT OF RICE AND BLACK ROT

BACKGROUND OF THE INVENTION

This invention relates to a method for controlling soft rot, bacterial seedling blight of rice and black rot by applying an *Erwinia carotovora* subsp. *carotovora*, particularly the *Erwinia carotovora* subsp. *carotovora* CGE234M403 strain (FERM BP-4328) alive to soil or plants.

Disease injuries of so-called soft rot caused by *Erwinia carotovora* develop in a large number of plants such as celery, head lettuce, carrot, Japanese radish, wasabi, potato, tobacco, tomato, cyclamen, etc. including Chinese cabbage and cabbage. As a method for controlling this soft rot, antibiotic preparations such as streptomycin, etc. and chemicals composed of copper compounds such as Bordeaux mixture have been mainly applied to date.

However, these chemicals not only give unsatisfactory control effects but also cause problems such as extinction of useful bacteria other than pathogenic bacteria, environmental contamination and chemical injuries. With respect to antibiotics, the appearance of bacteria having resistance to the same has become a problem.

In addition, there are a few pesticides which are now applicable to a method for controlling bacterial seedling blight of rice caused by *Pseudomonas plantarii* bacteria, so that a pesticide which can control the disease effectively is expected to be developed.

Furthermore, black rot caused by *Xathomonas campestris* pv. *campestris* develops in crops of Cruciferae such as cabbage, radish, broccoli, Chinese cabbage, etc. and its damage is serious. As a method for controlling this black rot, preventive spraying of copper wettable powder, organic copper wettable powder, Kasugamycin-copper wettable powder, copper hydroxy nonylbenzenesulfonate-copper wettable powder, copper-vinclozolin wettable powder and probenazole granules immediately after planting is carried out at present as a method of chemical pest control.

However, it is difficult to say that these chemicals give effective results. In addition, the appearance of resistant bacteria, environmental contamination, chemical injuries, etc. become problems. Accordingly, pesticides which are highly safe and raise no problem of environmental contamination are expected to be developed.

*Erwinia carotovora* is a bacterium causing so-called soft rot which softens and rots storage tissues of many plants such as Chinese cabbage, radish, etc. and is reported to exist in soil universally. Even in a field where a crop which serves as a host of this bacterium has not been grown for 5 years or more, there occasionally is a case where the occurrence of soft rot is observed. The ecological form of this bacterium is discussed in Hiroyuki Tsuyama, *Shokubutsu Boeki* (Plant Protection), vol. 34, pp. 294–298 (1980). In the case, for example, of Chinese cabbage, this bacterium grows around the root part of the plant on about the 40th day after seeding, and its existence comes to be observed in almost all the parts such as rhizosphere soil, top, etc. And, once chinese cabbage is injured by typhoon, insects, routine work, etc., the bacterium invades the site of injury, and if climatic conditions are right, the concentration of the pathogenic bacteria rises in only one night and lesions come to be observed. Therefore, if it becomes possible to grow nonpathogenic *Erwinia carotovora* instead of pathogenic ones in the rhizosphere soil and the top soil equally to the pathogenic strain, it can be expected that this will suppress the growth of the pathogenic bacterium and thus control soft rot. The present inventors made an intensive study on the basis of the above consideration. As a result of this study, they found that soft rot could be controlled effectively by selecting an *Erwinia carotovora* strain which not only grows well in competition with pathogenic strains of the *Erwinia carotovora,* but also has no pathogenicity. This strain was obtained from mutagenized strains of *Erwinia carotovora* and is applied to soil and plants as a microbial pesticide preparation containing this strain as an active ingredient. As a result of further studies, the inventors found that bacterial seedling blight of rice and black rot could also be controlled effectively by applying this microbial pesticide preparation to soil or plants. Thus, the inventors attained the present invention.

SUMMARY OF THE INVENTION

The present invention provides:

(1) An *Erwinia carotovora* subsp. *carotovora* CGE234M403 strain from which the pathogenicity of soft rot is deleted by mutagenesis.

(2) A controlling agent for soft rot which contains, as an active ingredient, the *Erwinia carotovora* subsp. *carotovora* CGE234M403 strain from which the pathogenicity of soft rot is deleted by mutagenesis.

(3). A method for controlling soft rot comprising applying, to soil or plants, the *Erwinia carotovora* subsp. *carotovora* CGE234M403 strain from which the pathogenicity of soft rot is deleted by mutagenesis.

(4) A method for controlling soft rot of a potato, comprising immersing tubers of a potato in a suspension containing the *Erwinia carotovora* subsp. *carotovora* CGE234M403 strain from which the pathogenicity of soft rot is deleted by mutagenesis, and planting the tubers of the potato into soil.

(5) A method for controlling soft rot of a potato, comprising dusting, over tubers of a potato, powder containing the *Erwinia carotovora* subsp. *carotovora* CGE234M403 strain from which the pathogenicity of soft rot is deleted by mutagenesis and planting the tubers of the potato into soil.

(6) A method for immobilizing bacteria as a controlling agent for soft rot comprising mixing, with saccharides or beef extract, *Erwinia carotovora* subsp. *carotovora* from which the pathogenicity of soft rot is deleted by mutagenesis and drying or freeze-drying the mixture under reduced pressure to immobilize the same.

(7) A method for controlling soft rot comprising mixing, with saccharides or beef extract, *Erwinia carotovora* subsp. *carotovora* from which the pathogenicity of soft rot is deleted by mutagenesis, drying or freeze-drying the mixture under reduced pressure to immobilize the same, dissolving the immobilized product in water and applying the same to plants.

(8) A controlling agent for soft rot which contains the *Erwinia carotovora* subsp. *carotovora* from which the pathogenicity of soft rot is deleted by mutagenesis and chemically synthesized water-soluble high molecular weight compounds, saccharides or protein.

(9) A controlling agent for bacterial seedling blight of rice which contains, as an active ingredient, *Erwinia*

*carotovora* subsp. *carotovora* from which the pathogenicity of soft rot is deleted by mutagenesis.

(10) A controlling agent for bacterial seedling blight of rice which contains *Erwinia carotovora* subsp. *carotovora* from which the pathogenicity of soft rot is deleted by mutagenesis and chemically synthesized water-soluble high molecular weight compounds, polysaccharides or protein.

(11) A method for controlling bacterial seedling blight of rice, comprising immersing rice seeds in a suspension containing the *Erwinia carotovora* subsp. *carotovora* from which the pathogenicity of soft rot is deleted by mutagenesis, and planting the rice seeds into soil.

(12) A method for controlling bacterial seedling blight of rice, comprising dusting, over rice seeds, powder containing *Erwinia carotovora* subsp. *carotovora* from which the pathogenicity of soft rot is deleted by mutagenesis and planting the rice seeds into soil.

(13) A method for controlling bacterial seedling blight of rice, comprising drenching or mixing a suspension, a powder or granules containing *Erwinia carotovora* subsp. *carotovora* from which the pathogenicity of soft rot is deleted by mutagenesis into nursery beds and planting rice seeds therein.

(14) A method for controlling bacterial seedling blight of rice, comprising spraying a suspension containing *Erwinia carotovora* subsp. *carotovora* from which the pathogenicity of soft rot is deleted by mutagenesis over the soil of nursery beds in which rice seeds are planted.

(15) A controlling agent for black rot which contains, as an active ingredient, *Erwinia carotovora* subsp. *carotovora* from which the pathogenicity of soft rot is deleted by mutagenesis.

(16) A controlling agent for black rot which contains *Erwinia carotovora* subsp. *carotovora* from which the pathogenicity of soft rot is deleted by mutagenesis and a chemically synthesized high molecular weight compound, polysaccharides or protein.

(17) A method for controlling black rot, comprising applying, to soil or plants, *Erwinia carotovora* subsp. *carotovora* from which the pathogenicity of soft rot is deleted by mutagenesis.

DESCRIPTION OF THE PREFERRED EMBODIMENTS

First, a method for preparing *Erwinia carotovora* subsp. *carotovora* from which the pathogenicity is deleted will be described hereinafter.

In order that a nonpathogenic Erwinia bacterium of the invention be able to grow in competition with pathogenic ones, it is advantageous for the non-pathogenic Erwinia to produce or to be engineered to produce an antibiotic effective against the pathogenic bacteria. As examples of such an antibiotic, bacteriocin, phage, etc. can be enumerated. With respect to bacteriocin produced by *Erwinia carotovora*, studies were made by Tsuyama, et al. [see Yoritsugu Endo, Hiroyuki Tsuyama, and Fusaji Nakatani; *Ann. Phytopath. Soc. Japan*, vol. 41, pp. 40–48 (1975)] and Takahashi, et al. [see Y. Itch, K. Izaki, and H. Takahashi, *J. Gen. Appl. Microbiol.*, vol. 24, pp. 27–39 (1978)]. These investigators purified a part of the bacteriocin and investigated its properties. When this bacterium is used as a pesticide, it is preferred that actions of these antibiotics such as bacteriocin and phage be effective against a broad range of pathogenic strains of *Erwinia carotovora*, and kill soft rot bacteria alone, not other bacteria useful for plants.

Therefore, the present inventors collected a large number of bacteria of *Erwinia carotovora* from vegetables which were healthy or carried lesions of soft rot and examined antibacterial activities of these bacteria to obtain some strains having antibacterial activities against a broad range of *Erwinia carotovora* strains. Among the obtained strains, the CGE234 strain is a promising strain, having a broad antibacterial spectrum and exhibiting low sensitivity to bacteriocin produced by other, related strains.

Bacterial properties of the CGE234 strain are given in Table 1.

TABLE 1

| | |
|---|---|
| Test on tubers of a potato | + |
| OF test | F |
| Indole test | − |
| Casein hydrolysis | − |
| Growth at 36° C. | + |
| Nitrate reduction | + |
| Anaerobic growth | + |
| Growth factor requirement | − |
| Acetoin production | + |
| Productivity of acid from saccharides | |
| Lactose | + |
| Inositol | + |
| Inulin | − |
| α-D-melibiose | + |
| D-sorbitol | − |
| Maltose | − |
| α-Methyl-D-glucoside | − |

Next, *Erwinia carotovora* was mutagenized to prepare a pathogenicity-deleted strain. As a method for mutagenesis, any method using generally available mutagenic agents, e.g., ethylmethanesulfonate, nitrosoguanidine, etc. and ultraviolet radiation [see "Manual of Methods for General Bacteriology", Gerhardt, P., et al (ed.), pp. 223–242, Washington, D.C., American Society for Microbiology (1981) or "Experimental Methods in Microbial Genetics", Tatsuo Ishikawa (ed.), pp. 3–32, Tokyo, Kyoritsu-Shuppan (1982)] is applicable. Mutagenesis may be carried out according to any of these methods.

The main factor for the development of pathogenicity in *Erwinia carotovora* is considered to be pectinase, particularly pectate lyase secreted by this bacterium [Masao Goto, "New Plant Bacterial Pathogenesis", p. 166, Tokyo Soft Science (1981)]. Therefore, screening for pathogenicity-deleted strains was performed by selecting strains having lowered pectinase secreting ability and subjecting the strains to a pathogenicity test using sections of Chinese cabbage. The pathogenicity test was performed by bruising leaf sections of Chinese cabbage, applying a highly concentrated solution of the bacteria to be screened thereto, leaving thus treated leaf sections stationary in a 28° C. controlled-temperature environment for 24 hours in the presence of moisture, and then measuring the length of lesions of the leaf sections.

Thus obtained pathogenicity-deleted *Erwinia carotovora* strains were mixed with pathogenic strains and then inoculated into bruised leaf sections of Chinese cabbage. As a result of this procedure, strains inhibiting the growth of the pathogenic strains, resulting in no lesions or drastically reducing the lesion-forming speed, were obtained.

Among these pathogenicity-deleted strains, strains having particularly high ability for inhibiting lesion formation were deposited in the National Institute of Bioscience and Human-technology, Agency of Industrial Science and Technology with the following accession numbers:

*Erwinia carotovora* subsp. *carotovora* CGE6M14 FERM P-10998

*Erwinia carotovora* subsp. *carotovora* CGE6M16 FERM P-10999

*Erwinia carotovora* subsp. *carotovora* CGE10M2 FERM P-11000

*Erwinia carotovora* subsp. *carotovora* CGE11M5 FERM P-11001

*Erwinia carotovora* subsp. *carotovora* CGE234M403 FERM BP-4328.

The present invention employs these pathogenicity-deleted *Erwinia carotovora* subsp. *carotovora*, preferably, the *Erwinia carotovora* subsp. *carotovora* CGE234M403 strain (FERM BP-4328). The bacteriological properties of this *Erwinia carotovora* subsp. *carotovora* CGE234M403 strain are identical with those of the parent strain, excluding the test on potato tubers, which is negative for *Erwinia carotovora* subsp. *carotovora* CGE234M403.

Hereinafter, a method for preparing the present microbial pesticides will be described.

First, pathogenicity-deleted *Erwinia carotovora* is incubated in a suitable medium. There is no particular restriction to the medium to be used as long as the bacteria can grow, so that ordinarily used media, e.g., 802 medium, nutrient medium, etc. (to be described later) may be used. After incubating the bacteria to grow at 20°–35° C. for about 10–35 hours, the culture solution was centrifuged to harvest the cells and thus to remove the medium ingredients. According to this procedure, the cells are concentrated, usually to a cell density of about $2 \times 10^{11}$–$3 \times 10^{11}$ cfu/ml.

The harvested cells are dried to immobilize them, using a protective agent, if necessary. As the immobilization protecting agent, saccharides comprising one or more of saccharose, glucose, fructose and sorbitol or beef extract are used. The immobilization is performed by mixing the protecting agent with the cells and then drying or freeze-drying the mixture under reduced pressure. As a specific example of this procedure, the harvested cells are suspended, e.g., in a protective liquid of 0.1M phosphate buffer (pH 7.0) containing 40% (w/w) saccharose and optionally containing 2% (w/w) sodium glutamate. This suspension is frozen and then dried for 3 days in a freeze dryer.

In the case of preparing a microbial pesticide using thus obtained dry cells, problems occasionally arise in dissolving the microbial pesticide in water and spraying the solution. Occasionally, the pesticide does not dissolve in water easily to become a homogeneous pesticide liquid and, depending on the preparation method of pesticide liquid, the pesticide becomes bead-shaped, thus lowering its wettability and thereby becomes very difficult to use.

Therefore, chemically synthesized water-soluble high molecular weight compounds, polysaccharides or protein may be mixed with the above dry cells in order to improve the wettability, according to demand. There is no particular restriction to the chemically synthesized water-soluble high molecular weight compounds so long as they can improve the wettability of the microbial pesticide. As specific examples of the above compounds, polyvinyl alcohol, polyethylene glycol, polyvinyl methyl ether, polyvinyl isobutyl ether, polyvinyl amine, polyvinyl pyrrolidone, polyethyleneimine, polyacrylamide, etc. can be enumerated. These can be used not only independently, but also in combination. Among these, polyvinyl alcohol and/or polyethylene glycol are preferable. In addition, there is no particular restriction to the polysaccharides and protein to be used so long as they can improve the wettability of the microbial pesticide. As specific examples of these, polysaccharides such as chitin, chitosan, agar, gum arabic, starch, soluble starch, dextrin, alpha starch, sodium alginate, tragacanth gum, locust bean gum, etc. and protein such as gelatin, casein, etc. can be enumerated. These can be used not only independently but also in combination. Among these, one or more selected from chitin, chitosan, agar, gum arabic and gelatin are preferable.

The present microbial pesticide can be manufactured into a preparation by adding and mixing a diluent, an auxilary, etc. according to demand. The dosage forms may be commonly adopted dosage forms such as powder, granules, wettable powder, etc., which may be selected suitably according to purpose.

As specific examples of the above diluent, diatomaceous earth, talc, clay, acid clay, bentonite, kaolin, wood flour, calcium carbonate, water, etc. can be enumerated. These can be used not only independently but also in combination.

As specific examples of the auxiliary, a surfactant, a stabilizer, a synergist for increasing the efficacy of other active ingredients, etc. can be enumerated. These can be used not only independently but also in combination.

It is preferred that the cell density of the preparation be adjusted to about $1 \times 10^6$–$1 \times 10^{11}$ cfu/g in the case of powder and granules and about $1 \times 10^6$–$1 \times 10^9$ cfu/g in the case of dissolving, wettable powder in water.

The mixing ratios of chemically synthesized water-soluble high molecular weight compounds, polysaccharides, protein, diluents, auxiliaries, etc. in preparing the present microbial pesticide may be selected suitably by considering various related matters such as properties of the microbial pesticide, kind of crops subject for application, the growth stage of the crops, etc. However, it is preferred that the content of the chemically synthesized water-soluble high molecular weight compounds, the polysaccharides or the protein in the microbial pesticide preparation be 5% (w/w) or more. A content of less than 5% (w/w) is not preferred because the wettability cannot be improved sufficiently by such concentration.

There is no particular restriction to the mixing ratio of the bacterium. However, it is preferable that the mixing ratio not be too low because that would make it necessary to apply a large quantity of pesticide in order to achieve sufficient control effects and might make the method uneconomical. The range of the mixing ratio is preferably 10–40% (w/w), more preferably 20–30% (w/w).

Hereinafter, the method for using the present microbial pesticide will be described.

For crops in which soft rot develops, the present microbial pesticide may be used in the same manner as commonly used pesticides. That is, it may be applied to soil or crops in which soft rot develops in the dosage form of powder or granules, or, in the case of wettable powder, by dissolving in a prescribed quantity of water.

The quantity of the pesticide preparation to be applied depends upon the cell density in the preparation. In the case of powder and granules, it is preferably about 1–100 g per liter of soil. In the case of using wettable powder by dissolving in water, it is preferably about 100 ml–400 liters per 10 ares.

In the case of using the present microbial pesticide for controlling soft rot of potatoes, it is effective to adopt a method comprising immersing potato tubers in a suspension containing the *Erwinia carotovora* subsp. *carotovora* CGE234M403 strain from which the pathogenicity of soft rot is deleted by mutagenesis and planting thus treated potato tubers in soil. There is no particular restriction to the time for immersing potatoes, and an adequate immersion time is 30 minutes or less to about 5–20 minutes. In certain circumstances, an appropriate effect can be recognized even by showering or spraying the tubers before or simultaneously with planting.

Hereinafter, a method for using the present microbial pesticide for the control of bacterial seedling blight of rice will be described.

In raising rice seedlings, various pesticides for the disinfection of seed-borne pathogenic microorganisms are used for controlling various plant diseases, e.g., bacterial grain rot of rice (seedling rot), bacterial seedling blight of rice, etc., which develop during the seedling raising period. There are several methods for using the pesticides such as: a method comprising immersing rice seeds in a pesticide liquid; a method comprising dusting pesticide powder over rice seeds; a method comprising drenching a pesticide liquid or mixing pesticide powder or granules into the soil of a nursery bed; and a method comprising spraying a pesticide liquid over the soil in which rice seeds are planted, etc. With respect to the present microbial pesticide containing the pathogenicity-deleted *Erwinia carotovora* as an active ingredient, any of these methods can be used.

In other words, the present microbial pesticide can be used by adopting methods such as: a method comprising immersing rice seeds in a suspension containing the pathogenicity deleted *Erwinia carotovora* and planting thus treated rice seeds in soil; a method comprising dusting powder containing the pathogenicity-deleted *Erwinia carotovora* over rice seeds and planting thus treated rice seeds in soil; a method comprising drenching or mixing a suspension, powder or granules containing the pathogenicity-deleted *Erwinia carotovora* into a nursery bed and planting rice seeds in the nursery bed; and a method comprising spraying a suspension containing the pathogenicity-deleted *Erwinia carotovora* over the soil of a nursery bed in which rice seeds are planted, etc.

In the case of the method comprising immersing rice seeds in a suspension containing the pathogenicity-deleted *Erwinia carotovora* and planting thus treated rice seeds in soil, there is no particular restriction to the time for immersing rice seeds in the suspension and thus the time may range from about 10 minutes to several days, if necessary, for seed soaking. In addition, the suspension may be mixed with a seed disinfectant at the time of seed soaking or seed disinfection, or before or after seed soaking.

In the case of the method comprising dusting powder containing the pathogenicity-deleted *Erwinia carotovora* over rice seeds and planting thus treated rice seeds in soil, there is no particular restriction to the time for dusting powder over rice seeds and thus the time may range from about 10 minutes to several days. The dusting may be carried out before or after seed soaking.

In the case of the method comprising drenching or mixing a suspension, a powder or granules containing the pathogenicity deleted *Erwinia carotovora* into a nursery bed and planting rice seeds in the nursery bed and a method comprising spraying a suspension containing the pathogenicity-deleted *Erwinia carotovora* over the soil of a nursery bed in which rice seeds are planted, it is preferred that the quantity of the present pesticide to be drenched, mixed or sprayed is about 1–100 g per liter of soil in the case of powder and granules and 10–1,000 ml in the case of a wettable powder suspension, though it depends upon the density of cells in the preparation.

In addition, the present microbial pesticide may be applied in the same manner as commonly used pesticides to crops such as cabbage, radish, Chinese cabbage, broccoli, etc. in which black rot develops. That is, it may be applied to soil or crops in which soft rot develops once to several times in the dosage form of powder or granules or, in the case of wettable water, by dissolving in the prescribed quantity of water. Furthermore, the present microbial pesticide can be applied preventively from the time immediately after planting.

It is preferred that the quantity of the present pesticide to be applied is about 100 g–50 kg per 10 ares in the case of powder and granules and about 100 ml –400 liters per 10 ares in the case of wettable powder suspension, though it depends upon the density of cells in the preparation.

EXAMPLES

Hereinafter, the present invention will be described by referring to examples. However, the present invention is not restricted to the following examples.

Certain references are cited in the application; certain prior filed applications are indicated in the Declaration. The entire disclosures of such references and applications are incorporated herein by reference.

The composition of media used in the examples is as follows:

802 Medium: Polypeptone 10 g, yeast extract 2 g, MgSO$_4$(7H$_2$O) 1 g, water 1 liter, pH 7.0 (In the case of plate culture, 15 g of agar is added.)

YCP Medium: (NH$_4$)$_2$SO$_4$ 2 g, MgSO$_4$(7H$_2$O) 0.2 g, Casamino acids 3 g, yeast extract 2 g, pectic acid 7 g, agar 15 g, water 1 liter, pH 8.0

Drigalski Lactose Agar Medium: Meat extract 4 g, lactose 10 g, Peptone 10 g, bromthymol blue 0.04 g, agar 16 g, water 1 liter, pH 7.4

Minimum Medium: NaHPO$_4$(7H$_2$O) 8.2 g, KH$_2$PO$_4$ 2.7 g, (NH$_4$)$_2$SO$_4$, 1.0 g, FeSO$_4$(7H$_2$O) 0.25 g, MgSO$_4$(7H$_2$O) 0.1 g, Ca(NO$_3$)$_2$, 5 mg. water 1 liter, pH 7.2

PG Medium: Pectic acid 5 g, NaNO$_3$ 1 g, K$_2$HPO$_4$ 4 g, MgSO$_4$(7H$_2$O) 0.2 g, agar 9 g, water 1 liter, pH 7.0

Nutrient Medium: Meat extract 3 g, peptone 10 g, NaCl 5 g, water 1 liter, pH 7.0

In Example 13 and after, the wettability of the present microbial pesticide was evaluated according to the following method, adopting solubility and dispersity as indices.

Method adopting solubility as an index:

Five hundred ml of distilled water was poured into a 1 liter beaker and stirred at a constant speed. Two grams of microbial pesticide was added with stirring to determine the time required for the solution to become a homogeneous suspension.

Method adopting dispersity as an index:

One hundred ml of distilled water was poured into a 100 ml beaker and left stationary. Two grams of microbial pesticide was dropped into the water to determine the time required for all the microbial pesticide to fall completely to the bottom of the beaker.

Example 1 (Method for Preparing Variant)

The *Erwinia carotovora* CGE234 strain was incubated in 802 medium at 30° C. until the middle period of the logarithmic growth phase. After adding 2 ml of a minimum medium to 2 ml of the culture solution, 2% ethylmethanesulfonate was added thereto, and the resulting culture solution was incubated for 80 minutes. After centrifuging the bacteria and washing the same once with 802 medium, 5 ml of fresh 802 medium was added, followed by overnight shake culture. 0.1 ml of culture solution was added to 5 ml of a PG medium and then incubated together with penicillin GK salt (the final concentration, 280 U/ml) at 30° C. for 6 hours. After diluting the culture, the dilution was smeared on an 802 medium plate and incubated overnight. After transplanting the culture to a YCP plate and further incubation overnight, 10% calcium chloride solution was added to the plate to select colonies producing small or substantially no pectinase halo. In this way, a variant CGE234M4 was obtained from the strain CGE234. Next, the CGE234M4 strain was further subjected to the same mutagenesis with ethylmethanesulfonate to obtain a variant CGE234M403 (FERM BP-4328). The CGE234M403 strain was incubated overnight in 802 medium and YCP medium to determine activities of this strain with pectate lyase, pectin lyase and polygalacturonase. It was found that the activities were all 0.01 U/OD-ml or lower.

Example 2 (Colonization)

1/2000-Wagner pots consisting of 3 groups of A, B and C were filled with volcanic ash soil and leaf mold in 2:1 ratio and 25 g each of (N:P:K=8:8:8) per pot as fertilizer. Chinese cabbages (Matsushima No. 2) were seeded and cultivated. On about the 30th day after seeding, 100 ml each of cell solution of the CGE234M403 strain ($1 \times 10^8$ cells/ml) was sprayed on roots and leaves. On the 63rd day and the 71st day after seeding, 1 cm² each of leaves and 1 g each of stems were collected, homogenized and diluted. The dilutions were smeared on plates containing Drigalski media to determine the cell concentration.

The cell concentrations on the leaves and in the stems are given in Table 2.

TABLE 2

|   |      | On the 63rd day after seeding | On the 71st day after seeding |
|---|------|------|------|
| A | Leaf | $4.0 \times 10^5/cm^2$ | $6.4 \times 10^3/cm^2$ |
|   | Stem | $1.2 \times 10^3/g$ | $1.3 \times 10^4/g$ |
| B | Leaf | $3.5 \times 10^4/cm^2$ | $7.8 \times 10^3/cm^2$ |
|   | Stem | $2.6 \times 10^3/g$ | $1.9 \times 10^4/g$ |
| C | Leaf | $4.2 \times 10^5/cm^2$ | $9.0 \times 10^4/cm^2$ |
|   | Stem | $6.5 \times 10^3/g$ | $2.8 \times 10^4/g$ |

As can be seen from Table 2, cells of the sprayed variant are stably colonized on leaves and in stems.

Example 3

Chinese mustard cultivated in a box was sprayed with 300 ml of a cell solution of the CGE234M403 strain ($1 \times 10^8$ cells/ml) about 30 days after seeding. 1 week after the spraying, 300 ml of a pathogenic bacterium ($1 \times 10^6$ cells/ml) was sprayed over the thus treated plants. The results of this treatment on the onset of disease on the 56th day after the seeding are given in Table 3.

TABLE 3

|   | Number of Stock Tested | Number of Stock with Lesions | Diseased Stock Percentage (%) | Disease Severity | Preventive Value (%) |
|---|---|---|---|---|---|
| No treatment | 12 | 7 | 58 | 39 | — |
| CGE234M403 | 12 | 2 | 17 | 11 | 72 |

Example 4

Chinese cabbages cultivated in an open field were sprayed with a cell solution of the CGE234M403 strain which was prepared to have a cell concentration of $1 \times 10^8$/ml, at a rate of 200 liters/10 ares. The spraying was carried out 3 times every week from about the 30th day after seeding. The results on controlling the onset of disease are given in Table 4. The results obtained by using Delan K manufactured by Yaesu Kagaku K.K. (500-fold dilution) as a control chemical are also given in the table.

TABLE 4

|   | Number of Stock Tested | Number of Stock with Lesions | Diseased Stock Percentage (%) | Disease Severity* | Preventive Value (%) |
|---|---|---|---|---|---|
| No treatment | 72 | 55 | 76.4 | 56.5 | — |
| Control Chemical | 72 | 34 | 47.2 | 32.4 | 42.7 |
| CGE234M403 | 70 | 19 | 27.1 | 14.3 | 74.6 |

$$*\text{Disease Severity} = \frac{\Sigma \text{ (Number of Diseased Stock according to } x \text{ Index)}}{\text{Total Number of Stocks Investigated} \times 3} \times 100$$

Index
0: A stock with no disease
1: A stock with diseases developed in only a part of its outer leaves. (It is possible to be shipped.)
2: A stock with diseases developed in only a part of its outer leaves and head forming leaves. (Although it is possible to be shipped as a small stock after removing the damaged parts, it falls under a grade A product.)
3: A stock with diseases developed in most part of its head forming leaves or with further damage. (It is impossible to be shipped.)

$$*\text{Preventive Value} = \frac{\text{Disease Severity for Untreated Stocks} - \text{Disease Severity for Stocks in Plot}}{\text{Disease Severity for Untreated Stocks}} \times 100$$

Example 5

The *Erwinia carotovora* CGE10M2 strain (FERM P-11000) was inoculated into 802 medium followed by 15 hours of incubation at 30° C. The cells were harvested from the culture solution using a centrifuge to obtain the cell concentrate (the concentration of cells was $3.0 \times 10^{11}$ cfu/ml). After mixing 25 μl of the cell concentrate with 25 μl of a protecting agent [40% (w/w) saccharose, 2% (w/w) sodium glutamate, 0.1M sodium phosphate buffer (pH 7.0)] thoroughly, the mixture was poured into an ampoule which was stoppered with absorbent cotton. After drying at 100 mtorr for 2.5 hours, the ampoule was sealed moltenly and kept at room temperature to examine changes with lapse of time.

As a result of this treatment, viable cell numbers after 10 days, 30 days and 90 days were 4% as compared with those before drying. In addition, samples were preliminarily frozen using a dry ice-ethanol freezing mixture prior to drying. As a result of this treatment, viable cell numbers after 10 days, 30 days and 90 days were respectively 39%, 35% and 35%, as compared with those before drying.

Furthermore, the results in the case of changing the saccharose concentration and in the case of adding no saccharose are given in Table 5.

Example 6

The cell survival ratios were determined in the same manner as in Example 5 except that glucose, fructose, sorbitol and beef extract of various concentrations were used instead of saccharose as a saccharide. The results are given in Table 6.

TABLE 6

| | Immobilization Protecting Agent | | | | Survival Ratio (%) | | |
|---|---|---|---|---|---|---|---|
| No. | (Saccharide) Saccharose (%) | Sodium Glutamate (%) | Sodium Phosphate Buffer (M) | Preliminary Freezing | 10 days | 30 days | 90 days |
| | Glucose | | | | | | |
| 1 | 20 | 2 | 0.1 | Not done | 13 | 2 | 5 |
| 2 | 30 | 2 | 0.1 | Not done | 13 | 4 | 3 |
| 3 | 20 | 2 | 0.1 | Done | 35 | 24 | 24 |
| 4 | 30 | 2 | 0.1 | Done | 62 | 60 | 63 |
| 5 | 40 | 2 | 0.1 | Done | 50 | 52 | 52 |
| 6 | 50 | 2 | 0.1 | Done | 49 | 49 | 47 |
| | Fructose | | | | | | |
| 7 | 20 | 2 | 0.1 | Not done | 7 | 4 | 4 |
| 8 | 30 | 2 | 0.1 | Not done | 8 | 5 | 3 |
| 9 | 20 | 2 | 0.1 | Done | 17 | 16 | 11 |
| 10 | 30 | 2 | 0.1 | Done | 40 | 34 | 24 |
| 11 | 40 | 2 | 0.1 | Done | 42 | 41 | 39 |
| 12 | 50 | 2 | 0.1 | Done | 25 | 23 | 23 |
| | Sorbitol | | | | | | |
| 13 | 20 | 2 | 0.1 | Not done | 29 | 20 | 13 |
| 14 | 30 | 2 | 0.1 | Not done | 28 | 24 | 6 |
| 15 | 20 | 2 | 0.1 | Done | 18 | 10 | 5 |
| 16 | 30 | 2 | 0.1 | Done | 25 | 25 | 31 |
| 17 | 40 | 2 | 0.1 | Done | 29 | 28 | 30 |
| 18 | 50 | 2 | 0.1 | Done | 18 | 18 | 17 |
| 19 | 60 | 2 | 0.1 | Done | 6 | 4 | 4 |
| | Beef Extract | | | | | | |
| 20 | 20 | 2 | 0.1 | Not done | 17 | 12 | 8 |
| 21 | 30 | 2 | 0.1 | Not done | 22 | 18 | 18 |
| 22 | 20 | 2 | 0.1 | Done | 9 | 5 | 2 |
| 23 | 30 | 2 | 0.1 | Done | 6 | 5 | 2 |

Example 7

A 32-cm-wide, 60-cm-long and 18-cm-high box was filled with a compost having a mixing ratio of volcanic ash soil to leaf mold of 2:1, followed by the transplanting of 12 seedlings of Chinese mustard. 10 days after transplanting, a cell immobilized product, which had been prepared by preserving the cell immobilized product given in No. 4 of Table 6 in Example 6 at room temperature for 10 days, was diluted with water to a volume of 60 ml and sprayed over the seedlings. The cell concentration at this time was $8.8 \times 10^7$ cfu/ml. 21 days after spraying, outer leaves of Chinese mustard were collected and subjected to determination of cell concentration. As a result of this treatment, $1.2 \times 10^4$ cfu/cm² of cells were colonized on the average.

TABLE 5

| | Immobilization Protecting Agent | | | | Survival Ratio (%) | | |
|---|---|---|---|---|---|---|---|
| No. | (Saccharide) Saccharose (%) | Sodium Glutamate (%) | Sodium Phosphate Buffer (M) | Preliminary Freezing | 10 days | 30 days | 90 days |
| 1 | 0 | 2 | 0.1 | Not done | 0 | 0 | 0 |
| 2 | 40 | 2 | 0.1 | Not done | 4 | 4 | 4 |
| 3 | 0 | 2 | 0.1 | Done | 0 | 0 | 0 |
| 4 | 10 | 2 | 0.1 | Done | 3 | 5 | 5 |
| 5 | 20 | 2 | 0.1 | Done | 17 | 9 | 10 |
| 6 | 30 | 2 | 0.1 | Done | 25 | 23 | 21 |
| 7 | 40 | 2 | 0.1 | Done | 39 | 35 | 35 |
| 8 | 50 | 2 | 0.1 | Done | 52 | 51 | 51 |
| 9 | 60 | 2 | 0.1 | Not done | 22 | 24 | 23 |

Example 8

Three seedlings of a Chinese cabbage were transplanted into the same box as in Example 7. A cell immobilized product, which had been prepared by making CGE234M403 (FERM BP-4328) into a preparation according to the method of No. 6 given in Table 5 in Example 5 and preserving the same at room temperature for 10 days, was diluted with water to a volume of 300 ml and was sprayed over the seedlings. The cell concentration at this time was $8.8 \times 10^7$ cfu/ml. 18 days after spraying, outer leaves of the Chinese cabbage were collected and cell concentration was determined. As a result of this treatment, $5.2 \times 10^3$ cfu/cm$^2$ were colonized. These seedlings were cultivated and harvested after 70 days, during which the onset of soft rot was not observed at all.

On the other hand, the onset of soft rot at the disease severity of 33.3 was observed in seedlings in the neighboring box which had not been sprayed with the cell immobilized product.

Disease Severity=[Σ (Number of Diseased Stock according to Degree of Disease×Index)/Total Number of Stocks Investigated×3]×100

Example 9

The CGE234M403 strain was incubated in a 10 liter jar fermenter for 36 hours using 4 liters of a medium prepared by adding glucose and polypeptone to nutrient medium. Subsequently, part of this culture was centrifuged to obtain 35 g of wet cells. After adding 40 g of 40% saccharose to the cells, the mixture was preliminarily frozen and then dried at 15 mtorr for 40 hours. 25 g of cell product was obtained. The viable cell concentration of this product at this time was $2.3 \times 10^{11}$ cfu/ml. This product was preserved at room temperature to examine its changes with the passage of time. As a result of this treatment, numbers of cells after 10 days, 30 days and 90 days were respectively 27%, 25% and 25%, as compared with those before drying.

Example 10

The *Erwinia carotovora* CGE234M403 strain (FERM BP-4328) was inoculated into 802 medium, followed by 15-hour incubation at 30° C. Cells were harvested from the culture using a centrifuge to obtain a cell concentrate (concentration of cells was $3.0 \times 10^{11}$ cfu/ml). After adding immobilization protecting agents [40% (w/w) saccharose, 2% (w/w) sodium glutamate and 0.1M sodium phosphate buffer (PH 7.0)] to the cell concentrate and freeze-drying the solution, the freeze-dried product was dissolved in water to prepare a treatment solution so adjusted as to have a cell concentration of $1 \times 10^8$ cfu/ml.

Tubers of a potato were halved, immersed in the above treatment solution and then planted to cultivate in Wagner pots (1/2,000 are). 48 days after planting, bacteria of soft rot were sprayed over the aboveground part at a concentration of $1 \times 10^7$ cfu/ml. 66 days after planting, the onset of soft rot was surveyed. The results were given in Table 7. The preventive value was 85%.

TABLE 7

|  | Stock No. | Number of Stems | Number of Diseased Stems | Ratio of Diseased Stems (%) |
|---|---|---|---|---|
| Untreated Plot | 1 | 3 | 3 | 71.5 |
|  | 2 | 5 | 2 |  |
|  | 3 | 6 | 5 |  |
| Treated Plot | 1 | 7 | 1 | 11.1 |
|  | 2 | 6 | 1 |  |
|  | 3 | 5 | 0 |  |

Example 11

After incubating the *Erwinia carotovora* CGE10M2 strain (FERM P-11000) in nutrient medium, tubers of a potato were treated in the same manner as in Example 10 and subjected to survey of the onset of soft rot. The results are given in Table 8. The preventive value was 75%.

TABLE 8

|  | Stock No. | Number of Stems | Number of Diseased Stems | Ratio of Diseased Stems (%) |
|---|---|---|---|---|
| Untreated Plot | 4 | 4 | 3 | 73.5 |
|  | 5 | 5 | 3 |  |
|  | 6 | 6 | 5 |  |
| Treated Plot | 4 | 5 | 2 | 18.7 |
|  | 5 | 6 | 1 |  |
|  | 6 | 5 | 0 |  |

Example 12

Tubers of a potato were halved and planted in Wagner pots. 41 days after planting, a freeze-dried product, which was prepared in the same manner as in Example 10, was diluted with water to prepare a cell suspension of the *Erwinia carotovora* CGE234M403 strain (FERM BP-4328) so adjusted as to have a cell concentration of $1 \times 10^8$ cfu/ml, and was then sprayed over pots at a rate of 100 ml/pot. After 48 days passed, bacteria of soft rot were sprayed at a concentration of $1 \times 10^7$ cfu/ml. 66 days after planting, the onset of soft rot was surveyed. The results are given in Table 9. The preventive value was 84%.

TABLE 9

|  | Stock No. | Number of Stems | Number of Diseased Stems | Ratio of Diseased Stems (%) |
|---|---|---|---|---|
| Untreated Plot | 7 | 5 | 4 | 75.0 |
|  | 8 | 5 | 4 |  |
|  | 9 | 6 | 4 |  |
| Treated Plot | 7 | 6 | 0 | 11.8 |
|  | 8 | 6 | 1 |  |
|  | 9 | 5 | 1 |  |

Example 13

The *Erwinia carotovora* CGE234M403 strain (FERM BP-4328) was inoculated into nutrient medium, followed by 20-hour incubation at 30° C. Cells were harvested using a centrifuge to obtain a cell concentrate (the concentration of cells was $3.0 \times 10^{11}$ cfu/ml). Then, the cell concentrate was suspended in a protective solution of 0.1M phosphate buffer (pH 7.0) containing 40% (w/w) saccharose and then freeze-dried to prepare dry cells as the main ingredient of the microbial pesticide. 100 parts by weight of this freeze-dried *Erwinia carotovora* strain, 240 parts by weight of diatomaceous earth. 20 parts by weight of calcium carbonate and 40 parts by weight of polyvinyl alcohol were mixed to prepare a microbial pesticide.

The wettability of the thus prepared microbial pesticide was evaluated, adopting solubility and dispersity as indices. The results are given in Table 10.

Example 14

A microbial pesticide was prepared in the same manner as in Example 13 except that polyethylene glycol was used instead of polyvinyl alcohol and the wettability thereof was evaluated in the same manner as in Example 13. The results are given in Table 10.

Comparative Example 1

A microbial pesticide was prepared in the same manner as in Example 13, except that sodium ligninsulfonate as a surfactant was used instead of polyvinyl alcohol and the wettability thereof was evaluated in the same manner as in Example 13. The results are given in Table 10.

Comparative Example 2

A microbial pesticide was prepared in the same manner as in Example 13, except that carboxymethyl cellulose as a surfactant was used instead of polyvinyl alcohol and the wettability thereof was evaluated in the same manner as in Example 13. The results are given in Table 10.

Comparative Example 3

A microbial pesticide was prepared in the same manner as in Example 13 except that polyvinyl alcohol was not added, and the wettability thereof was evaluated in the same manner as in Example 13. The results are given in Table 10.

TABLE 10

| | Additive [% (w/w)] | Solubilization Time (min.) | Dispersion Time (min.) |
|---|---|---|---|
| Example 13 | Polyvinyl alcohol (10) | 1.5 | 4.0 |
| Example 14 | Polyethylene glycol (10) | 2.0 | 7.0 |
| Comparative Example 1 | Sodium ligninsulfonate | 13.0 | 18.0 |
| Comparative Example 2 | Carboxymethyl cellulose | 13.5 | 17.5 |
| Comparative Example 3 | No additive | 15.0 or more | 20.0 or more |

Example 15

The *Erwinia carotovora* CGE234M403 strain (FERM BP-4328) was inoculated into a nutrient medium, followed by 20-hour incubation at 30° C. Cells were harvested using a centrifuge to obtain a cell concentrate (the concentration of cells was $3.0 \times 10^{11}$ cfu/ml). Then, the cell concentrate was suspended in a protective solution of 0.1M phosphate buffer (pH 7.0) containing 40% (w/w) saccharose and then freeze-dried to prepare dry cells as the main ingredient of the microbial pesticide. 100 parts by weight of this freeze-dried *Erwinia carotovora* strain, 200 parts by weight oil diatomaceous earth, 20 parts by weight of calcium carbonate and 80 parts by weight of polyvinyl alcohol were mixed to prepare a microbial pesticide.

The wettability of the thus prepared microbial pesticide was evaluated adopting solubility and dispersity as indices. The results are given in Table 11.

Example 16

A microbial pesticide was prepared in the Same manner as in Example 15 except that polyethylene glycol was used instead of polyvinyl alcohol, and the wettability thereof was evaluated in the same manner as in Example 15. The results are given in Table 11.

Comparative Example 4

A microbial pesticide was prepared in the same manner as in Example 15, except that polyvinyl alcohol was not added and the wettability thereof was evaluated in the same manner as in Example 15. The results are given in Table 11.

TABLE 11

| | Additive [% (w/w)] | Solubilization Time (min.) | Dispersion Time (min.) |
|---|---|---|---|
| Example 15 | Polyvinyl alcohol (20) | 1.0 | 4.0 |
| Example 16 | Polyethylene glycol (20) | 1.0 | 3.7 |
| Comparative Example 4 | No additive | 15.0 or more | 20.0 or more |

Example 17

The *Erwinia carotovora* CGE234M403 strain (FERM BP-4328) was inoculated into nutrient medium, followed by 20-hour incubation at 30° C. Cells were harvested using a centrifuge to obtain a cell concentrate (the concentration of cells was $3.0 \times 10^{11}$ cfu/ml). Then, the cell concentrate was suspended in a protective solution of 0.1M phosphate buffer (pH 7.0) containing 40% (w/w) saccharose and then freeze-dried to prepare dry cells as the main ingredient of the microbial pesticide. 100 parts by weight of this freeze-dried *Erwinia carotovora* strain, 240 parts by weight of diatomaceous earth, 20 parts by weight of calcium carbonate and 40 parts by weight of chitin were mixed to prepare a microbial pesticide.

The wettability of the thus prepared microbial pesticide was evaluated adopting solubility and dispersity as indices. The results are given in Table 12.

Example 18

A microbial pesticide was prepared in the same manner as in Example 17, except that chitosan was used instead of chitin, and the wettability thereof was evaluated in the same manner as in Example 17. The results are given in Table 12.

Example 19

A microbial pesticide was prepared in the same manner as in Example 17, except that agar was used instead of chitin, and the wettability thereof was evaluated in the same manner as in Example 17. The results are given in Table 12.

Example 20

A microbial pesticide was prepared in the same manner as in Example 17, except that gum arabic was used instead of chitin and the wettability thereof was evaluated in the same manner as in Example 17. The results are given in Table 12.

Example 21

A microbial pesticide was prepared in the same manner as in Example 17, except that gelatin was used instead of chitin, and the wettability thereof was evaluated in the same manner as in Example 17. The results are given in Table 12.

Comparative Example 5

A microbial pesticide was prepared in the same manner as in Example 17, except that sodium ligninsulfonate as a surfactant was used instead of chitin, and the wettability thereof was evaluated in the same manner as in Example 17. The results are given in Table 12.

Comparative Example 6

A microbial pesticide was prepared in the same manner as in Example 17, except that carboxymethyl cellulose as a surfactant was used instead of chitin, and the wettability thereof was evaluated in the same manner as in Example 17. The results are given in Table 12.

Comparative Example 7

A microbial pesticide was prepared in the same manner as in Example 17 except that chitin was not added, and the wettability thereof was evaluated in the same manner as in Example 17. The results are given in Table 12.

TABLE 12

| | Additive [% (w/w)] | Solubilization Time (min.) | Dispersion Time (min.) |
|---|---|---|---|
| Example 17 | Chitin (10) | 1.0 | 3.5 |
| Example 18 | Chitosan (10) | 0.5 | 5.0 |
| Example 19 | Agar (10) | 1.3 | 4.0 |
| Example 20 | Gum arabic (10) | 2.0 | 5.0 |
| Example 21 | Gelatin (10) | 0.5 | 7.0 |
| Comparative Example 5 | Sodium ligninsulfonate | 13.0 | 18.0 |
| Comparative Example 6 | Carboxymethyl cellulose | 13.5 | 17.5 |
| Comparative Example 7 | No additive | 15.0 or more | 20.0 or more |

Example 22

The *Erwinia carotovora* CGE234M403 strain (FERM BP-4328) was inoculated into a nutrient medium, followed by 20-hour incubation at 30° C. Cells were harvested using a centrifuge to obtain a cell concentrate (the concentration of cells was $3.0 \times 10^{11}$ cfu/ml). Then, the cell concentrate was suspended in a protective solution of 0.1M phosphate buffer (pH 7.0) containing 40% (w/w) saccharose and then freeze-dried to prepare dry cells as the main ingredient of the microbial pesticide. 100 parts by weight of this freeze-dried *Erwinia carotovora* strain, 200 parts by weight of diatomaceous earth, 20 parts by weight of calcium carbonate and 80 parts by weight of chitin were mixed to prepare a microbial pesticide.

The wettability of the thus prepared microbial pesticide was evaluated, adopting solubility and dispersity as indexes. The results are given in Table 13.

Example 23

A microbial pesticide was prepared in the same manner as in Example 22, except that chitosan was used instead of chitin, and the wettability thereof was evaluated in the same manner as in Example 22. The results are given in Table 13.

Example 24

A microbial pesticide was prepared in the same manner as in Example 22, except that agar was used instead of chitin, and the wettability thereof was evaluated in the same manner as in Example 22. The results are given in Table 13.

Example 25

A microbial pesticide was prepared in the same manner as in Example 22, except that gelatin was used instead of chitin, and the wettability thereof was evaluated in the same manner as in Example 22. The results are given in Table 13.

Example 26

A microbial pesticide was prepared in the same manner as in Example 22, except that gum arabic was used instead of chitin, and the wettability thereof was evaluated in the same manner as in Example 22. The results are given in Table 13.

Comparative Example 8

A microbial pesticide was prepared in the same manner as in Example 22 except that chitin was not added and the wettability thereof was evaluated in the same manner as in Example 22. The results are given in Table 13.

TABLE 13

| | Additive [% (w/w)] | Solubilization Time (min.) | Dispersion Time (min.) |
|---|---|---|---|
| Example 22 | Chitin (20) | 0.5 | 0.5 |
| Example 23 | Chitosan (20) | 0.3 | 3.0 |
| Example 24 | Agar (20) | 0.8 | 3.5 |
| Example 25 | Gum arabic (20) | 1.8 | 10.0 |
| Example 26 | Gelatin (20) | 0.5 | 7.0 |
| Comparative Example 8 | Sodium ligninsulfonate | 15.0 or more | 20.0 or more |

Example 27

The *Erwinia carotovora* CGE234M403 strain (FERM BP-4328) was inoculated into 802 medium, followed by hour incubation at 30° C. Cells were harvested using a centrifuge to obtain a cell concentrate (the concentration of cells was $3.0 \times 10^{11}$ cfu/ml). The cell solution prepared to contain immobilizing agent [40% (w/w) saccharose, 2% (w/w) sodium glutamate and 0.1M sodium phosphate buffer; pH 7.0] was freeze-dried and then dissolved in water to prepare a suspension so adjusted as to have a cell density of $1 \times 10^8$ cfu/ml.

Rice seeds infected with a pathogenic bacterium of bacterial seedling blight of rice were immersed in the above cell suspension for 3 days. After changing the cell suspension for a new one and immersing the rice seeds for 3 more days, the thus treated rice seeds were seeded. In the control plot, the same operations were performed using water instead of the cell suspension. The above operations were both performed at a solution temperature of 15° C., and the temperature was raised to 30° C. for the following one day in order to forcibly sprout the rice seeds. One month after planting, the onset of bacterial seedling blight of rice was surveyed to obtain the results given in Table 14. The preventive value was 100%.

TABLE 14

| Plot | Number of Seedlings | Number of Diseased Seedlings | Ratio of Diseased Seedlings | Preventive Value |
|---|---|---|---|---|
| Control Plot | 466 | 209 | 44.8 | — |
| CGE234M03 Plot | 452 | 0 | 0.0 | 100.0 |

Example 28

A cell suspension (the cell concentration was $1 \times 10^8$ cfu/ml) of the *Erwinia carotovora* CGE234M403 strain (FERM BP-4328) prepared in the same manner as in Example 27 was sprayed over the nursery bed soil at a rate of 100 ml/liter of soil, in which rice seeds infected with a pathogenic bacterium of bacterial seedling blight of rice were seeded. In the control plot, the same operations were performed using water instead of the cell suspension. The above operations were both performed at a temperature of 15° C., and the temperature was raised to 30° C. for the following one day in order to forcibly sprout the rice seeds. 15 days after seeding, the onset of bacterial seedling blight of rice was surveyed to obtain the results given in Table 15. The preventive value was 96.3%.

TABLE 15

| Plot | Number of Seedlings | Number of Diseased Seedlings | Ratio of Diseased Seedlings | Preventive Value |
|---|---|---|---|---|
| Control Plot | 89 | 53 | 59.6 | — |
| CGE234M03 Plot | 92 | 2 | 2.2 | 96.3 |

Example 29

The *Erwinia carotovora* CGE234M403 strain (FERM BP-4328) was inoculated into a nutrient medium, followed by 15 hour incubation at 30° C. Cells were harvested using a centrifuge to obtain a cell concentrate (the concentration of cells was $3.0 \times 10^{11}$ cfu/ml). The cell concentrate was mixed with immobilizing agents (40% (w/w) saccharose and 0.1M sodium phosphate buffer, pH 7.0), freeze-dried and then dissolved in water to prepare a suspension so adjusted as to have a cell density of $1 \times 10^8$ cfu/ml. Similarly, a suspension of the *Erwinia carotovora* CGE10M2 strain (FERM P-11000) was prepared.

10 days after planting of cabbages in pots, the suspensions (the cell concentration was $1 \times 10^8$ cfu/ml) of the *Erwinia carotovora* subsp. *carotovora* CGE234M403 strain and CGE10M2 strain were sprayed over the cabbages. On the 7th day after planting, bacteria of black rot (the CGX2 strain, the cell concentration was $1 \times 10^8$ cfu/ml) were sprayed over the cabbages. On the 30th day after spraying, the onset of black rot was surveyed. The results are given in Table 16. The preventive values were 71.5% and 57.1% respectively for the CGE234M403 strain and the CGE10M2 strain.

TABLE 16

| Plot | Number of Cabbage Stocks | Ratio of Diseased Stocks | Preventive Value | Ratio of Diseased Leaves | Preventive Value |
|---|---|---|---|---|---|
| Control Plot | 12 | 75.0 | — | 58.3 | — |
| CGE234M403 Plot | 12 | 25.0 | 66.7 | 16.7 | 71.4 |
| CGE10M2 Plot | 12 | 41.7 | 44.4 | 25.0 | 57.1 |

Example 30

The *Erwinia carotovora* CGE234M403 strain (FERM BP-4328) was inoculated into nutrient medium, followed by 15 hour incubation at 30° C. Cells were harvested using a centrifuge to obtain a cell concentrate (the concentration of cells was $3.0 \times 10^{11}$ cfu/ml). Then, the cell concentrate was mixed with immobilizing agents (40% (w/w) saccharose and 0.1M sodium phosphate buffer, pH 7.0), freeze-dried and then dissolved in water to prepare a suspension so adjusted as to have a cell concentration of $1 \times 10^8$ cfu/ml.

The cell suspension (the cell concentration was $1 \times 10^8$ cfu/ml) of the *Erwinia carotovora* subsp. *carotovora* CGE234M403 strain was sprayed over pot culture broccoli on the 10th day after planting. On the 7th day after spraying, black rot bacteria (the CGX2 strain, the cell concentration was $1 \times 10^8$ cfu/ml) was sprayed over the broccoli. On the 30th day after spraying of the bacteria, the onset of black rot was surveyed. The results are given in Table 17. The preventive value was 90.9%.

TABLE 17

| Plot | Number of Broccoli Stocks | Ratio of Diseased Stocks | Preventive Value | Ratio of Diseased Leaves | Preventive Value |
|---|---|---|---|---|---|
| Control Plot | 10 | 80.0 | — | 15.4 | — |
| CGE234M403 Plot | 10 | 10.0 | 87.5 | 1.4 | 90.9 |

What is claimed is:

1. An *Erwinia carotovora* subsp. *carotovora* CGE234M403 strain from which the pathogenicity of soft rot is deleted by mutagenesis.

2. An agent for controlling soft rot or for controlling bacterial seedling blight of rice or for controlling black rot, which contains, as an active ingredient, *Erwinia carotovora* subsp. *carotovora* CGE234M403 strain from which the pathogenicity of soft rot is deleted by mutagenesis.

3. A method for controlling soft rot, comprising applying, to soil or a plant, *Erwinia carotovora* subsp. *carotovora* CGE234M403 strain from which the pathogenicity of soft rot is deleted by mutagenesis.

4. The method for controlling soft rot according to claim 3, in which the plant is a potato and in which the *Erwinia carotovora* subsp. *carotovora* CGE234M403 strain is applied by immersing tubers of a potato in a suspension containing said strain, and planting the tubers into soil.

5. The method for controlling soft rot according to claim 3, in which the plant is a potato and in which the *Erwinia carotovora* subsp. *carotovora* CGE234M403 strain is applied by dusting powder containing said strain over tubers of a potato, and planting the tubers into soil.

6. A method for immobilizing bacteria of soft rot, comprising mixing, with a saccharide or beef extract,

*Erwinia carotovora* subsp. *carotovora* CGE234M403 from which the pathogenicity of soft rot is deleted by mutagenesis and drying or freeze-drying the resulting mixture under reduced pressure to immobilize the same.

7. The method for immobilizing bacteria of soft rot according to claim 6, wherein the saccharide is selected from the group consisting of saccharose, glucose, fructose and sorbitol.

8. A method for controlling soft rot, comprising mixing, with a saccharide or beef extract, *Erwinia carotovora* subsp. *carotovora* CGE234M403 from which the pathogenicity of soft rot is deleted by mutagenesis, drying or freeze-drying the resulting mixture under reduced pressure to immobilize the mixture, dissolving the immobilized mixture in water and applying the mixture to a plant.

9. The method for controlling soft rot according to claim 8, wherein the saccharide is selected from the group consisting of saccharose, glucose, fructose and sorbitol.

10. The agent for controlling soft rot or for controlling bacterial seedling blight of rice or for controlling black rot, according to claim 2, further comprising a chemically synthesized water-soluble high molecular weight compound, a saccharide or a protein.

11. The agent according to claim 10, in which the saccharide is selected from the group consisting of saccharose, glucose, fructose and sorbitol.

12. A method for controlling bacterial seedling blight of rice, comprising applying, to rice seeds, *Erwinia carotovora* subsp. *carotovora* CGE234M403 from which the pathogenicity of soft rot is deleted by mutagenesis.

13. The method for controlling bacterial seedling blight of rice according to claim 16, in which *Erwinia carotovora* subsp. *carotovora* CGE234M403 is applied by immersing rice seeds in a suspension containing *Erwinia carotovora* subsp. *carotovora* CGE234M403 from which the pathogenicity of soft rot is deleted by mutagenesis, and planting the rice seeds into soil.

14. The method for controlling bacterial seedling blight of rice according to claim 12, in which *Erwinia carotovora* subsp. *carotovora* CGE234M403 from which the pathogenicity of soft rot is deleted by mutagenesis is applied by dusting powder containing said *Erwinia carotovora* subsp. *carotovora* CGE234M403 over rice seeds, and planting the rice seeds into soil.

15. The method for controlling bacterial seedling blight of rice according to claim 12, in which *Erwinia carotovora* subsp. *carotovora* CGE234M403 from which the pathogenicity of soft rot is deleted by mutagenesis is applied by drenching or mixing a suspension, powder or granules containing said *Erwinia carotovora* subsp. *carotovora* CGE234M403 into nursery beds, and planting rice seeds therein.

16. The method for controlling bacterial seedling blight of rice according to claim 12, in which *Erwinia carotovora* subsp. *carotovora* CGE234M403 from which the pathogenicity of soft rot is deleted by mutagenesis is applied by spraying a suspension containing said *Erwinia carotovora* subsp. *carotovora* CGE234M403 over the soil of nursery beds in which rice seeds are planted.

17. A method for controlling black rot, comprising applying, to soil or a plant, *Erwinia carotovora* subsp. *carotovora* CGE234M403 from which the pathogenicity of soft rot is deleted by mutagenesis.

* * * * *